United States Patent [19]

Meldal

[11] Patent Number: 5,352,756
[45] Date of Patent: Oct. 4, 1994

[54] POLY(ETHYLENE OR PROPYLENE GLYCOL)-CONTAINING POLYMER

[75] Inventor: Morten P. Meldal, Maalov, Denmark

[73] Assignee: Carlsberg A/S, Copenhagen, Denmark

[21] Appl. No.: 75,758

[22] Filed: Jun. 11, 1993

Related U.S. Application Data

[63] Continuation-in-part of Ser. No. 835,277, Feb. 13, 1992, abandoned.

[51] Int. Cl.$^5$ .................... C08G 63/48; C08G 63/12
[52] U.S. Cl. ................................ 525/50; 525/539; 528/296; 528/304; 528/312; 528/320
[58] Field of Search ............. 525/50, 539; 528/296, 528/304, 312, 320

[56] References Cited

U.S. PATENT DOCUMENTS

| | | | |
|---|---|---|---|
| 4,644,038 | 2/1987 | Protzman | 525/412 |
| 4,977,228 | 12/1990 | Wakabayashi et al. | 528/901 |
| 5,087,690 | 2/1992 | Demarey | 528/230 |
| 5,130,405 | 7/1992 | Walker et al. | 528/78 |

OTHER PUBLICATIONS

Daniels, S. B. et al. "Membranes as Solid ... " Tetrahedron Letters, 1989, vol. 30, No. 33, pp. 4345–4348.GB.
Small, P. et al. "Design and Application of a New ... " Journal of the Chemical Society, Chemical Communications, 1989, No. 21, pp. 1589–1591.
Meldal, M. "Pega: A Flow Stable Polyethylene ... " Tetrahedron Letters, 1992, vol. 33, No. 21, pp. 3077–3080 G.B.

Primary Examiner—John Kight, III
Assistant Examiner—Terressa Mosley
Attorney, Agent, or Firm—Ladas & Parry

[57] ABSTRACT

A crosslinked poly(ethylene or propylene)glycol-containing polymer which has a unique spatial structure and can be designed especially for application as a chromatographic resin or as a solid support for the synthesis of peptides, oligonucleotides or oligosaccharides or as a substrate for the immobilization of proteins. The polymer is formed by radical copolymerization of derivatized poly(ethylene or propylene) glycol bis-end substituted with a moiety selected from the group consisting of acryloylalkyl, acryloylaryl, acrylamidoalkyl and acrylamidoaryl with an acrylic amide, nitrile or ester. When it is to be used as a solid support or immobilization substrate, the polymer will incorporate a spacer comprising functional groups for the attachment of peptides, proteins, nucleotides or saccharides such as those selected from the group consisting of amino, alkylamino, hydroxy, carboxyl, mercapto, sulfeno, sulfino, sulfo and derivatives thereof.

21 Claims, 4 Drawing Sheets $n = 45$, $m = 6$
$R^6 = -CO-N(CH_3)_2$

POLY(ETHYLENE OR PROPYLENE GLYCOL)-CONTAINING POLYMER

This is a continuation-in-part of copending application(s) Ser. No. 07/835,277 filed on Feb. 13, 1992, now abandoned and International Application PCT/DK93/0051 filed on Feb. 12, 1993.

This invention relates to a crosslinked poly(ethylene or propylene)glycol-containing polymer which has a unique spatial structure and can be designed especially for application as a chromatographic resin or as a solid support for the immobilization of proteins or for the synthesis of peptides, oligonucleotides or oligosaccharides.

BACKGROUND OF THE INVENTION

When solid phase peptide synthesis was first introduced by Bruce Merrifield[1] it was performed on a support of 2% cross linked polystyrene allowing the preparation of a pentapetide by a batchwise synthesis protocol, This invention formed the basis of a technique, which has since been subjected to continuous refinement. With the synthesis of longer peptides it soon became apparent that the cross linking of the resin had to be optimized. The best results were obtained with the 1% Gross linked resin still used in the batch synthesis today[2]. A more polar dimethyl acrylamide resin suitable for peptide synthesis in polar solvents like DMF was developed in Sheppards laboratory[3].

With the introduction of Fmoc-based solid phase synthesis[4,5] the much more efficient continuous flow process became a realistic alternative to the batch method. The available batch resins were however not flow stable and collapsed after a few synthesis cycles. It was well established that increased cross linking while increasing the stability of the resin would not lead to useful properties for peptide synthesis. The first flow stable synthesis resin was obtained by polymerization of the soft polydimethyl acrylamide gel inside a solid matrix of supporting kieselguhr[6]. This ingenious invention allowed the packing of columns, which were completely flow stable throughout the synthesis. The principle was refined by replacing the irregular kieselguhr with a more regular rigid 50% cross linked polystyrene sponge containing a grafted polydimethyl acrylamide gel[7].

At the same time a technique was developed for grafting polyethylene glycol on to a 1% crosslinked polystyrene[8]. The resulting resins were monodisperse, spherical and, more importantly, flow stable. A more controlled grafting by direct substitution of the functional groups in the polystyrene with modified polyethylene glycol carrying an amino group has also been described[9]. Polystyrene grafted to films of polyethylene has been used for synthesis of peptides under nonpolar conditions[10] and polyhydroxypropyl acrylate coated polypropylene[11] and the natural polymer, cotton, has shown some promise as supports under polar conditions[12].

A preparation of a polymer with short crosslinking PEG chains (n=6) was attempted by inverse suspension polymerization of polyethylene glycol methacrylate macromonomers[13]; but with the high PEG content (60% crosslinker) the polymer became semicrystalline already during the polymerization reaction. The described polymer of short chain PEG crosslinked by means of ester linkages[13] was not suited for peptide synthesis.

SUMMARY OF THE INVENTION

The present invention provides a novel crosslinked poly(ethylene or propylene)glycol-containing polymer designed especially for application as a flow stable, highly polar solid support for solid phase synthesis. The polymer was constructed to be stable under continuous flow conditions and to be transparent with no absorbance in the aromatic region to allow the spectrophotometric monitoring of reaction within the resin. It should furthermore form a highly branched polymer network, with good swelling in polar solvents allowing uncomplicated assembly of even long peptides. The change in swelling should be insignificant throughout the synthesis, and the density of the resin should allow multiple column peptide synthesis. Therefore the resin was designed to be highly polar assisting peptide solvatization, allowing penetration of polar components into the interior of the beads and preventing adherence to plastics. Finally easy preparation and low cost starting materials were considered to be very important for a successful synthesis resin.

This is achieved with the polymer according to the invention which is formed by radical copolymerization of a derivatized poly(ethylene or propylene)glycol of the formula

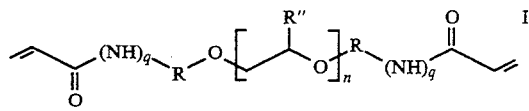

wherein n is an integer of from 4 to 2,000, q is zero or 1, R'' is H or $CH_3$, and R is

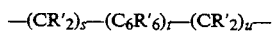

where s, t and u each is zero or an integer of 1-10, and each R' is H, alkyl, aralkyl, substituted aralkyl, aryl or substituted aryl, said substituted aralkyl and substituted aryl being ring substituted with alkyl, hydroxy, mercapto, nitro, amino, mono- or dialkylamino, or halogen, with an acrylic compound of the formula

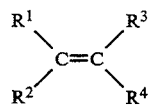

wherein $R^1$ is —CY—X—$R^5$ or —CN, and $R^2$, $R^3$ and $R^4$ each is H, alkyl, aralkyl, aryl, —CY—X—$R^5$ or —CN, where Y is O or S, X is O, S or $NR^6$ $R^5$ is alkyl aralkyl or aryl and $R^6$ is H or $R^5$, and optionally with a spacer molecule comprising functional groups for the attachment of peptides, proteins, nucleotides or saccharides.

When it is to be used as a solid support for the synthesis of peptides, oligonucleotides or oligosaccharides or as a substrate for the immobilization of proteins, the polymer according to the invention will incorporate a spacer comprising functional Groups for the attachment of peptides, proteins, nucleotides or saccharides such as those selected from the Group consisting of amino, alkylamino, hydroxy, carboxyl, mercapto, sulfeno, sulfino, sulfo and derivatives thereof.

A polymer according to the invention which is especially suited for application as a solid support for continuous flow or batchwise synthesis of peptides, oligonucleotides or oligosaccharides is formed by copolymerization of a derivatized poly(ethylene or propylene)-glycol of the formula I, wherein n, q, R″ and R are as defined above with an acrylamide of the formula

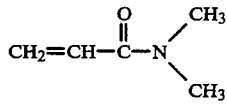

and with a spacer molecule of the formula

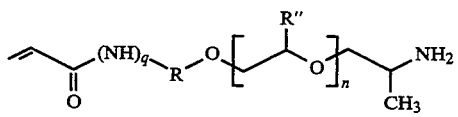

wherein n, q, R″ and R are as defined for formula I above.

Preferred values of n in formula I above are between about 20 and about 90, i.e. the compound is a derivative of $PEG_{900}$ to $PEG_{4000}$ or of $PPG_{1200}$ to $PPG_{5300}$. Preferred values of n in formula II are between about 4 and about 45, i.e. the compound is a derivative of $PEG_{200}$ to $PEG_{2000}$ or of $PPG_{250}$ to $PPG_{2600}$.

A preferred polymer according to the invention is composed of 60% of 0,0′-bis-(2-acrylamidoprop-1-yl)-$PEG_{900}$ (1), 20% of 0-(2-acrylamidoprop-1-yl)-0′-(2-aminoprop-1-yl)-$PPG_{300}$ (2) and 20% of N,N-dimethyl acrylamide (3).

Such polymers according to the invention may again be derivatized with any of the linkers normally used in peptide synthesis. Four well characterized linkers for peptide synthesis are 4-[fluorenylmethyloxycarbamido(2,4-dimethoxyphenyl)methyl]phenoxyacetic acid of the formula

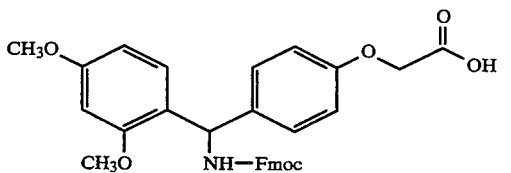

and 4-hydroxymethylphenoxyacetic acid[20] which are both cleaved in TFA producing peptide amides and peptide acids, respectively, 4-hydroxymethylbenzamide[20] which with 0.1 M NaOH, and 4-hydroxymethyl-3-nitrobenzamide[2] which is cleaved by photolysis. The compound 4 is also called 4-[Fmoc-amino(2,4-dimethoxyphenyl)methyl]phenoxyacetic acid where "Fmoc" signifies "fluorenylmethyloxycarbonyl".

The present invention also relates to a solid support for continuous flow or batchwise synthesis of peptides, oligonucleotides or oligosaccharides said support comprising a polymer according to the invention as described above. A particular feature of the support according to the invention is that it is also suitable for syntheses involving enzymatic reactions.

The invention also relates to a solid support for enzymatic synthesis of oligosaccharides with glycosyltransferases said support comprising a polymer according to the invention as described above.

Further, the invention relates to a solid support for the immobilization of proteins said support comprising a polymer according to the invention as described above.

Still further, the invention relates to a resin for application in chromatographic separations such as Gel-permeation chromatography and ion-exchange chromatography said resin comprising a polymer according to the invention as described above.

The present invention also relates to a method of continuous flow or batchwise synthesis of peptides, oligonucleotides or oligosaccharides wherein the peptide, oligonucleotide or oligosaccharide during the synthesis is attached to a solid support comprising a polymer according to the invention as described above and at the end of the synthesis is cleaved from said solid support. Due to the particular features of the polymer according to the invention this method also lends itself to syntheses involving enzymatic reactions and specifically to an enzymatic synthesis of an oligosaccharide with a glycosyltransferase.

The invention also relates to a method of immobilizing a protein wherein the protein is attached to a solid support comprising a polymer according to the invention as described above.

Further, the invention relates to a method of performing chromatographic separations which comprises the use of a chromatographic resin comprising a polymer according to the invention as described above.

In the following the polymer according to the invention is for short termed the PEGA resin or PEGA polymer.

THE STRUCTURE OF THE PEGA RESIN

Figure 1:
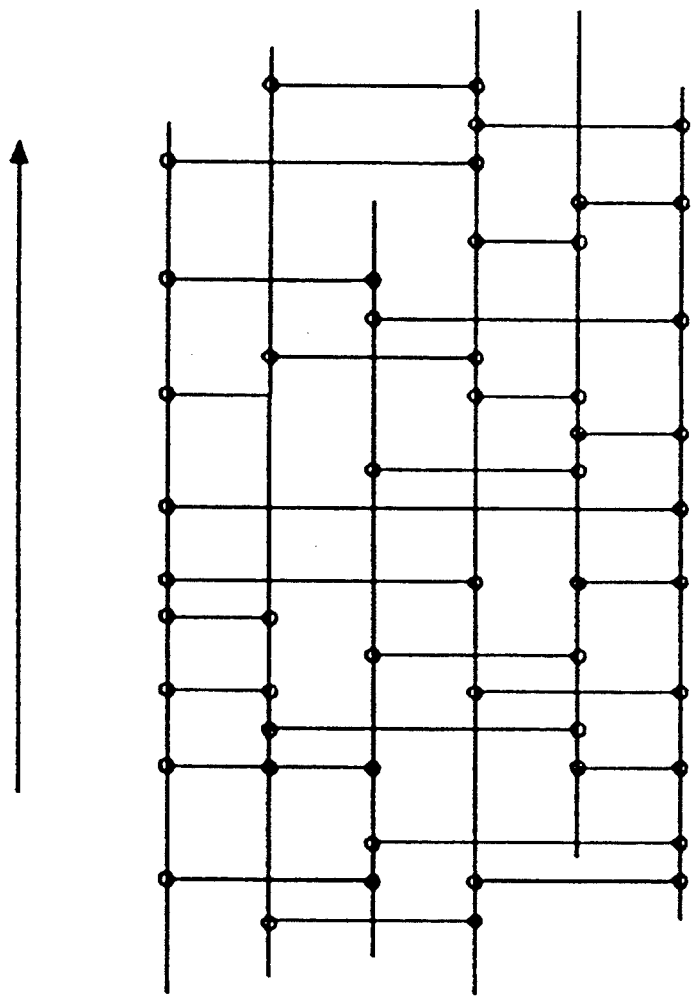
FIG. 1 is a schematic representation of the PEGA polymer where the polyacrylamide backbones are shown vertically and the crosslinking PEG moieties are shown horizontally.

The PEGA polymer has a unique structure compared with other polymers due to the extremely high content of crosslinking long chain PEG. The polymer form a highly and uniformly branched network of very long flexible interweaving chains which allows a high degree of swelling to a specific and very well defined bead size. The structure may be described by the schematic representation shown in FIG. 1 where the polyacrylamide backbones are shown vertically and the cross-linking PEG moieties are shown horizontally. Branch points are indicated by a dot.

The good swelling and the long and flexible chains yield a gel-like and yet hard polymer with very Good diffusion properties in the comb-like interior. The very high content and dominating influence of the PEG on the properties of the polymer yield a resin which swells equally well in polar solvents, e.g. water, N-N-dimethyl formamide, acetonitrile and trifluoroacetic acid, and unpolar solvents, e.g. dichloromethane and chloroform.

Figure 4:
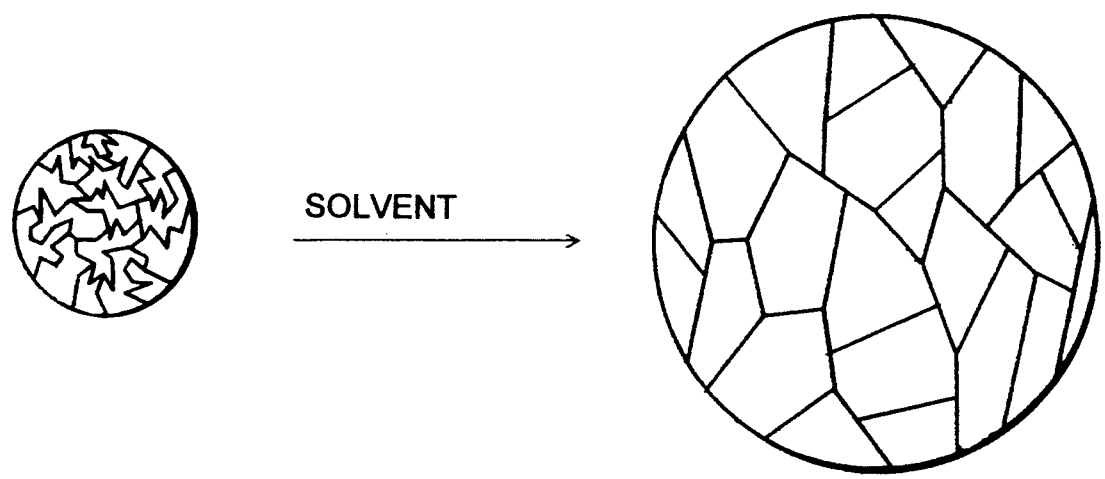
FIG. 4 illustrates the large but limited swelling of the PEGA polymer.

Thus, the base and acid stable polymer according to the present invention is characterized by its very powerful swelling potential in many solvents of very different polarity (e.g. $CH_2Cl_2$ or water), derived from the high solvation energy of the major polymer component, polyoxyethylene (PEG) in these solvents. This amphipathic nature of PEG is due to its flexibility and ability to form folded structures with either polar or hydrophobic surfaces. The use of a high content (60–70%) of well defined diacrylamido-PEG for the crosslinking of the polymer result in a uniform and relatively large swelling volume (e.g. 13 fold the volume of the dry polymer with PEG 1900) in most solvents. The principle of the large, but limited swelling is demonstrated in FIG. 4 where the folded PEG is behaving as folded springs which are stretched out completely by the large force of PEG solvation to form a completely permeable polymer with large and uniform internal cavities allowing for mass transport and chemical reactions to be carried out inside the polymer with kinetic parameters similar to those observed in solution.

The extremely polar character, the swelling in water and the large pores of the gel-like polymer allows the use of enzymes in reactions on the support. Thus it was demonstrated that a $\beta$-1-4-galactosyltransferase could transfer galacto-syl-UDP to a resin bound N-acetyl glucosamine. These properties are currently being further evaluated.

Figure 2:
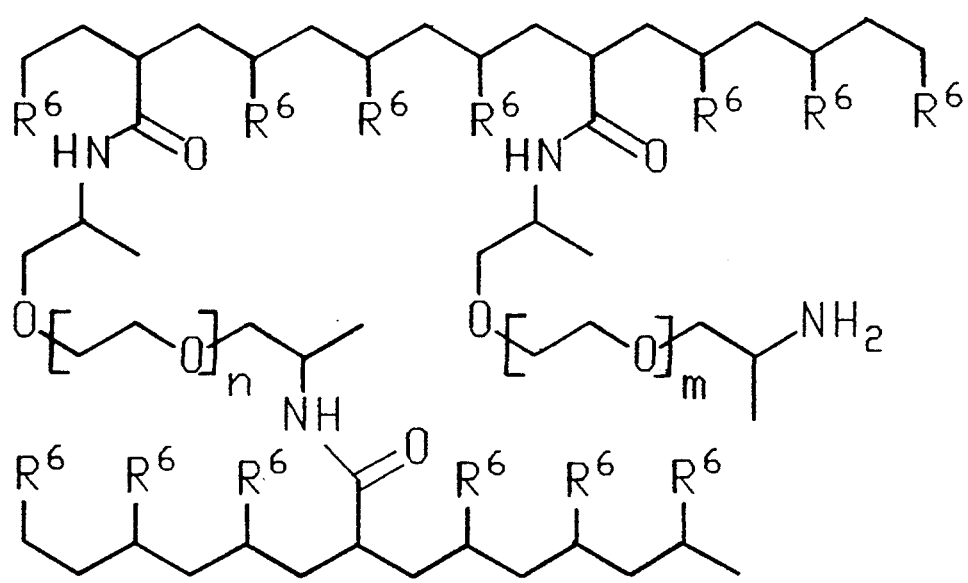
FIG. 2 illustrates a fragment of the chemical structure of the PEGA polymer.

A fragment of the chemical structure of the polymer is presented in FIG. 2. Other types of spacers can be derivatized with acryloyl chloride and incorporated to introduce the functional group, which can be an amino group, a carboxylic, phosphonic or sulfonic acid group, a mercapto or a hydroxy group, into the resin. Alternatively it may be omitted completely for a non functionalized resin. This can for example be applied in gel permeation chromatography, and the resin with charged groups can be applied in ion exchange chromatography. This is possible because this resin in contrast to other gel resins of the polydimethyl acrylamide and the polystyrene type is flow stable.

The process for producing the polymer of the invention is unique in that an aminofunctionalized, flow stable, highly swelling polymer with a constant swelling volume is obtained in a single radical polymerization step. The application of the efficient acrylamide-based radical polymerization allow the formation of completely uniform spherical beads with a narrow size distribution (175–200 μm) needed for fast solid phase chemical reactions carried out in the flow through mode. The polymer contains no ester bonds, and this is a requirement for a polymer which is used in a variety of chemical reactions involving strong and nucleophilic bases (e.g. piperidine or aqueous solutions of alkali metal hydroxides) as well as strong acids (e.g. trifluoroacetic acid or HF).

EXAMPLE 1

Copolymerization of 0,0'-bis-(2-acrylamidoprop-1-yl)-$PEG_{1900}$ (1), 0-(2-acrylamidoprop-1-yl)-0'-(2-aminoprop-1-yl) -$PPG_{300}$ (2) and N,N-dimethyl acrylamide (3) afforded a resin which fulfilled most of the above criteria.

Compound 1 was prepared in 67% yield by reaction of 0,0'-bis-(2-aminoprop-1-yl)-polyethylene glycol 1900 (available from Fluka Chemie AG, Switzerland, under the trade name "Jeffamine ® ED-2001") dissolved in dichloromethane and triethylamine (2 eqv.) at 0° C. with acryloylchloride (2 eqv.). The mixture was filtered after 30 min and concentrated to half the volume. Diethyl ether (4 volumes) was added and the product crystallized with a small amount of $Et_3N \cdot HCl$. It was collected by filtration, washed with diethyl ether, dried and characterized by $^1H$-NMR spectroscopy.

A similar procedure with dropwise addition of acryloylchloride (1 eqv.) to triethylamine and 0,0'-bis-(2-aminoprop-1-yl)-polypropylene glycol 300 (available from Fluka Chemie AG, Switzerland, under the trade name "Jeffamine ® D-400") in dichloromethane was employed for the preparation of compound 2. The product could not be crystallized but was stirred several times with diethyl ether at 20° C. and decanted after cooling to −30° C. Residual diethyl ether was removed in vacuo yielding 74% of product containing one acrylamido- and one amino group for each PPG molecule according to the integration of a $^1H$-NMR spectrum.

$^1H$-NMR in $CDCl_3$ relative to $CHCl_3 = 7.30$ ppm, δ ppm(J Hz) for 1; Acrylamide; 6.33 (17,0, 2H, $CH_2$-trans), 5.64(10.0,2H, $CH_2$-cis), 6.19(17.0, 10.0, 2H, CH); 2-amidopropyl; 1.24(6.6, 6H, $CH_3$); 4.19–4.16(m, 2H, CH) 3.50(6.6, 10.6,$CH_2$) 3.66(m, 190H, PEG), 2 had similar chemical shifts and integrated correctly.

$Et_3N \cdot HCl$ could be removed from I by partition between $CH_2Cl_2$ and water. The bisacrylamido-$PPG_{300}$ is insoluble in water and can therefore be removed from 2 before polymerization. The syrup was estimated to contain approximately 15% of respectively the bisacrylamido- and the diamino-$PPG_{300}$-derivatives.

The polymer was prepared in a granulated and in a beaded form both with a high content of PEG and with 20% N,N-dimethyl acrylamide added to avoid neighboring branching points in the acrylic polymer. The 20% of the mono amine 3 was added to yield a substitution of approximately 0.1 mmol/ml in the final swollen resin. Thus 1 (3 g), 2 (1 g) and 3 (1 mL) were dissolved in DMF (5 mL) and water (3 mL). The solution was purged with argon for 15 min. Ammonium peroxydisulfate (800 mg) in water (2 mL) was added. The solution was stirred for 5 min and then left for 5 h to polymerize. It was cut up and granulated through a fine stainless steel net with mask size 0.8 mm. Fines were decanted 3 times with ethanol (100 mL). It was washed on a filter with water (100 mL), sodium hydroxide (1 M, 50 mL), water (200 mL), DMF (50 mL), and ethanol (100 mL) and sucked dry. The resin was lyophilized affording 84% yield. The granulated resin swelled to 6 mL/g in DMF. It was swelling to a similar degree in dichloromethane, in TFA, in alcohols and in water, thus showing a wide scope for applications.

Alternatively the resin was prepared in a beaded form essentially as described by Kanda et al.[14]. The beaded polymer was treated as described above yielding 70% of fine beads swelling to 8 mL/g in DMF. The beaded resin was best handled as a slurry in DMF since the dry beads had a tendency to adhere to glass and metal. It did however not at all adhere to plastics and teflon.

The beaded resin (200 mg) was packed into a glass column and derivatized with Fmoc-Gly-O-Pfp and then 4-[Fmoc-amino(2,4-dimethoxyphenyl)methyl]phenoxyacetic acid,(4; Rink linker[15], 160 mg) by the TBTU procedure[16]. After 20 min Dhbt-OH was added indicating complete reaction, and acetic anhydride (40 μl) was added. The resin was deprotected and the test decapeptide fragment from acyl carrier protein 65–74 (5; FIG.

Figure 3:
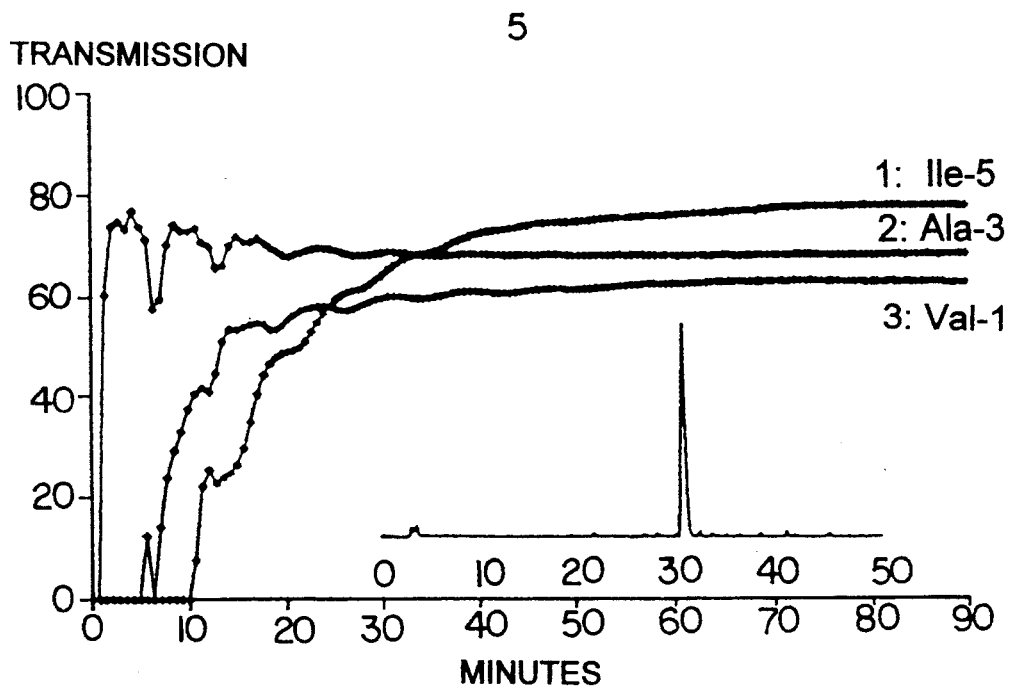
FIG. 3 illustrates at the top the sequence 5 of the test decapeptide fragment from acyl carrier protein 65-74 synthesized in the Example and below it a Graph presenting transmission spectra of three of the acylation reactions and a HPLC trace of the crude product.

3) was synthesized by the Dhbt ester method[17] on a custom made peptide synthesizer the reaction being followed with a solid phase spectrophotometer[18]. In FIG. 3 transmission curves are shown for three of the acylation reactions. The peptide was isolated in 31 mg crude product yield by cleavage with 92% TFA, 3% anisole, 1% EDT, 1% thioanisole and 3% $H_2O$. The recorded reaction times were compared to the reaction times for the same synthesis on the kieselguhr supported polyamide resin[19] presented in brackets: Gly, 2 min; Asn, 3 min (30 min); Ile, 43 min (60 min); Tyr, 3 min (36 min); Asp, 3 min (20 min); Ile, 73 min (30 min), Ala, 5 min (20 min); Ala, 5 min (20 min); Gln, 10 min (60 min); Val, 65 min (>1,440 min). The last addition of Val to Gln is known to be particularly difficult due to aggregation in the resin allowing complete acylations only with precautions and addition of hydrogen bond breaking agents. With the PEGA resin it was complete in 65 min, and HPLC and amino acid analysis and sequence analysis showed no presence of the desvaline peptide usually observed in these syntheses. Similar reaction times and results were obtained with the granulated resin.

EXAMPLE 2

Preparation of a beaded 1900/300-PEGA Resin 0,0′-bis-(2-acrylamidoprop-1-yl)-$PEG_{1900}$        (1)

0,0′-bis-(2-aminoprop-1-yl)-PEG1900 ("Jeffamine ® ED-2001"; 300 g, 150 mmol, 300 mmol $NH_2$) was dissolved in triethylamine (41,7 ml, 300 mmol) and dichloromethane (350 ml) and acroylchloride (24.37 ml, 300 mmol) was slowly added with cooling at 0°–15° C. over a period of 40 min with efficient stirring. Then the mixture was stirred for 20 min. After filtration and washing with $CH_2Cl_2$ (100 ml) the combined filtrate was evaporated at 10 and 0.1 torr (40° C). $Et_2O$ (800 mL) was added. The product was stirred and then cooled and allowed to crystallize at −78° C. with stirring and then left overnight at −20° C. Filtration and grinding up with more $Et_2O$ (500 ml) followed by filtration and washing with $Et_2O$ (300 ml) afforded 308 g of product.

0-(2-acrylamidoprop-1-yl)-0′-(2-aminoprop-1-yl)-$PPG_{300}$        (2)

0,0′-bis-(2-aminoprop-1-yl)-$PPG_{300}$ ("Jeffamine ® D-400"; 100 ml, 0.5 mole $NH_2$-groups) was dissolved in $CH_2Cl_2$ (50 ml) and acroylchloride (10 ml, 0.12 mole) dissolved in $CH_2Cl_2$ (150 ml) was slowly added under argon at 0° C. with cooling on ice over a period of 90 min. The mixture was stirred for 20 min and evaporated first at 10 torr and then at 0.1 torr to yield a thick syrup. This crude mixture was used for the polymerization.

Polymerization 1 (150 g) and 2 (100 g) were dissolved in water (570 ml) stirring with a stream of argon. N,N-Dimethylacrylamide (fresh, 30 g) was added and flushing was continued for 5 min. Hexane (1685 ml) and $CCl_4$ (1,140 ml) were mixed in the polymerization apparatus and argon was flushed through. The apparatus was heated to 65°–77° C. $(NH_4)_2S_2O_8$ (4.2 g) in $H_2O$ (15 ml) was added to the aqueous polymerization mixture at 20° C. with argon stirring. Sorbitan monolaurate (3.6 g in 15 ml DMF) was added and the mixture was transferred to the apparatus stirring 550–600 rpm (T=50° C). After 2 min stirring at 550 rpm N,N,N′,N′-tetramethyl ethylenediamine (12 ml) was added and the stirring was continued while the temperature was increased to 65° C. After 30 min the stirring was increased to 600 rpm and continued for 4 h. The resin was cooled and filtered in a 12 cm * 35 cm filter with a valve, washed with methanol (1 L) and water (2 L). It was passed through a steelnet, transferred back to the filter and washed with water (8 L) and methanol (2.5 L). The methanol may be removed by lyophilization.

USE OF THE PEGA RESIN FOR SOLID-PHASE SYNTHESIS

General Procedure

Synthesis of the glycopeptides was performed in DMF with a custom-made, fully automatic, continuous-flow peptide synthesizer or by the plastic syringe technique (as described below) using PEGA-resin{358} (0.07 mmol/g). Amino acids were coupled as their Pfp esters (3 equiv.) with DhbtOH (1 equiv.) added as an auxiliary nucleophile or as their Dhbt-esters (3 equiv.). The sidechains were protected with $Bu^t$ for serine, threonine and tyrosine. $N^\alpha$-Fmoc deprotection was effected by treatment with 20% piperidine in DMF for 30 min and the acylation times were determined with a solid-phase spectrophotometer at 440 nm. Glycine was coupled directly on to the resin followed by coupling of the Rink-linker by the TBTU procedure.{413} The first amino acid was coupled and unchanged amino groups were capped by addition of acetic anhydride before coupling of the second amino acid. After deprotection of the last amino acid the resin was removed from the column, washed with dichloromethane and lyophilized overnight. The cleavage of the peptide or the glycopeptide from the solid support was performed by treatment with a mixture of TFA, water and scavengers as described in detail under the individual peptides. After cleavage the resin was poured on to a glass filter and washed three times with TFA followed by 95% aqueous acetic acid. The combined filtrates were concentrated and the residue was solidified by several triturations with diethylether which was decanted. Residual solvent was removed under reduced pressure and the peptide was purified by preparative HPLC.

The purified acetylated glycopeptide was dissolved in dry methanol (1 mg $cm^{-3}$) and 1 mol $dm^{-3}$ sodium methoxide in methanol was added until a wetted pH-paper indicated pH 11. The mixture was stirred at ambient temperature for 2 h, neutralized with small pieces of solid $CO_2$ and concentrated. The residue was dissolved in water (1 mg $cm^{-3}$) and purified by preparative HPLC.

Plastic syringe technique

Peptide 28 and glycopeptide 29 were synthesized by use of the plastic syringe technique, which is a simple and cheap alternative to automatic peptide synthesizers. The technique is exemplified here with the synthesis of dipeptide, H-Asn-Phe-$NH_2$ 28. A 20 $cm^3$ disposable plastic syringe A (without piston) was fitted with a sintered teflon filter (pore size 70 μm) and the outlet connected to the outlet of a 50 $cm^3$ plastic syringe B via a teflon tube with luer adapters. Syringe B was used as a waste syringe to remove solvents. PEGA-resin (0.5 g, 0.07 mmol/g) was placed in syringe A and allowed to swell in DMF (10 $cm^3$) which was carefully added from the top and removed from the bottom by suction with syringe B. $N^\alpha$-Fmoc-L-Gly-OPfp (49 mg, 0.105 mmol)

and DhbtOH (5.7 mg, 0.035 mmol) was dissolved in DMF (4 cm³) and the mixture poured on to the resin. After coupling the resin was rinsed with DMF (8×4 cm³) before N$^\alpha$-Fmoc deprotection. Piperidine in DMF (20%, 2×4 cm³) was added to the resin in two steps. The first portion was sucked quickly through the resin followed by addition of the second portion, which was removed after 30 min. After thorough rinse with DMF (8×4 cm³) Rink-linker (57 mg, 0.105 mmol), TBTU (34 mg, 0.105 mmol) and N-ethyl-morpholine (26 mm³, 0.21 mmol) was dissolved in DMF (4 cm³) and added to the resin. After 2 h the resin was rinsed with DMF (8×4 cm³) before N-Fmoc deprotection and coupling of N$^\alpha$-Fmoc-L-Phe-OPfp and N$^\alpha$-Fmoc-L-Asn-OPfp as described above. After final deprotection the peptide-resin was rinsed with dichloromethane and lyophilized before cleavage of the peptide from the solid support with TFA/ethanedithiol/thioanisol/anisol/water (67/1/1/2.7/2.7) to yield crude dipeptide 28.

H-Asn-Phe-NH$_2$ 28 and H-Asn(2,3,6-tri-O-acetyl-4-O-(2, 3,4,6-tetra-O-acetyl-$\beta$-D-galactopyranosyl)-$\beta$-D-glucopyranosyl)Phe-NH$_2$ 29.—Title compounds 28 and 29 were synthesized by the plastic syringe technique as described. In the synthesis of 29 H-Phe-Resin was coupled with 27 (80 mg, 0.07 mmol) to give peptide-resin A.

d-Ala-Ser-Thr-Thr-Thr-Asn(4-O-$\alpha$-D-glucopyranosyl-$\beta$-D-glucose)-Tyr-Thr-NH$_2$ 31.—The solid-phase synthesis was carried out on a custom-made, fully automatic, continuous-flow peptide synthesizer, according to the general procedure as described above. PEGA-resin (0.5 g, 0.07 mmol/g) was used. Two equivalents of 7 (80 mg, 0.07 mmol) were used, with one equivalent of Dhbt-OH (5.7 mg, 0,035 mmol). After completed coupling (4 h) residual 7 was recovered (48 mg, 0.04 mmol). d-Alanine was incorporated as the free acid by the TBTU procedure. {413} After cleavage from the resin with TFA/ethanedithiol/thioanisol/anisol/water (67/1/1/2.7/2.7) (22 cm³, 2 h, ambient temperature) and trituration with ether, the solidified crude glycopeptide, hepta-O-acetate 30 (36 mg, 87% - based on 7) was purified by preparative HPLC using 10% solvent B for 20 min, followed by a linear gradient of 10–60% solvent B during 100 min (retention time 59.6 min). The yield of 30 was 11 mg (27%). Deacetylation with sodium methoxide as described above, followed by purification by preparative HPLC using 0% solvent B for 10 min, followed by a linear gradient of 0–30% solvent B during 60 min (retention time 30.6 min) afforded pure title compound 31 (5.5 mg, 17%). $^1$H and $^{13}$C NMR data are presented in Table 7 and Table 8, respectively. Amino acid analyses (theoretical value in parenthesis): Ala 1.00 (1), Asn 0.88 (1), Ser 1.06 (1), Thr 4.17 (4), Tyr 0.89 (1).

TABLE 7

$^1$H-NMR chemical shifts (ppm) and coupling constants (Hz) of 32$^a$ and 31$^b$, measured at 500 MHz and 600 MHz at 300K. Reference: Internal acetic acid at 2.03 ppm.

| | | 32 | 31 | | | 32 | 31 |
|---|---|---|---|---|---|---|---|
| ala$^1$ | $\alpha$ | 4.160 (7.0) | 4.162 (7.1) | Asn$^6$ | N$^\alpha$H | 8.325 (8.0) | 8.371 (7.6) |
| | $\beta$ | 1.536 | 1.539 | | $\alpha$ | 4.694 | 4.742 |
| Ser$^2$ | N$^\alpha$H | 8.690 (6.8) | 8.708 (6.9) | | $\beta$ | 2.762 (6.5; 15.5) | 2.848 (6.2; 16.1) |
| | $\alpha$ | 4.560 | 4.568 | | $\beta'$ | 2.669 (7.5) | 2.762 (7.1) |
| | $\beta$ | 3.911 (5.5; 11.5) | 3.911 (5.9; 11.5) | | N$^\gamma$H | 7.489 | 8.791 (8.8) |
| | $\beta^1$ | 3.864 (5.0) | 3.868 (5.2) | | N$^\gamma$H' | 6.819 | — |
| Thr$^3$ | N$^\alpha$H | 8.306 (8.0) | 8.325 (7.8) | Tyr$^7$ | N$^\alpha$H | 8.183 (7.0) | 8.205 (7.0) |
| | $\alpha$ | 4.464 (4.5) | 4.471 (4.3) | | $\alpha$ | 4.600 | 4.603 |
| | $\beta$ | 4.279 (6.5) | 4.284 (6.5) | | $\beta$ | 3.045 (7.5; 14.0) | 3.052 (7.0; 14.0) |
| | $\gamma$ | 1.202 | 1.206 | | $\beta'$ | 2.961 (8.0) | 2.969 (8.0) |
| Thr$^4$ | N$^\alpha$H | 8.183 (7.0) | 8.215 (7.5) | | $\delta, \delta'$ | 7.110 (8.5) | 7.114 (8.4) |
| | $\alpha$ | 4.421 (4.5) | 4.430 (4.6) | | $\epsilon, \epsilon'$ | 6.807 | 6.812 |
| | $\beta$ | 4.230 (6.5) | 4.243 (6.4) | Thr$^8$ | N$^\alpha$H | 7.977 (8.0) | 8.029 (8.0) |
| | $\gamma$ | 1.177 | 1.179 | | $\alpha$ | 4.230 (4.0) | 4.240 |
| Thr$^5$ | N$^\alpha$H | 8.100 (7.5) | 8.119 (7.6) | | $\beta$ | 4.204 (6.5) | 4.212 (6.3) |
| | $\alpha$ | 4.297 (4.5) | 4.298 (4.7) | | $\gamma$ | 1.130 | 1.143 |
| | $\beta$ | 4.108 (6.5) | 4.097 (6.3) | | CONH | 6.968 | 6.978 |
| | $\gamma$ | 1.095 | 1.088 | | CONH' | 7.030 | 7.063 |

| | H-1 | H-2 | H-3 | H-4 | H-5 | H-6 | H-6' |
|---|---|---|---|---|---|---|---|
| 31 $\alpha$-D-glucopyranosyl | 5.367 (3.8) | 3.561 (9.8) | 3.672 (9.5) | 3.395 (9.5) | 3.697 | 3.864 (11.4) | 3.748 |
| $\beta$-D-glucopyranose | 4.90$^c$ | 3.389 (9.2) | 3.798 (8.7) | 3.625 | 3.743 | 3.832 (1.7; 12.2) | 3.738 (5.1) |

$^a$5.2 mg in 10% CD$_3$COOD/H$_2$O (600 mm³, pH 2.27).
$^b$4.6 mg in 10% CD$_3$COOD/H$_2$O (600 mm³, pH 2.41).
$^c$Approximate value.

TABLE 8

Selected $^{13}$C-NMR chemical shifts (ppm) of 32$^a$ and 31$^b$, measured at 125.77 MHz at 300K. Reference: Internal acetic acid at 20.0 ppm.

| | | 32 | 31 | | | 32 | 31 |
|---|---|---|---|---|---|---|---|
| ala$^1$ | $\alpha$ | 49.5 | 49.6 | Asn$^6$ | $\alpha$ | 50.5 | 50.2 |
| | $\beta$ | 16.8 | 16.9 | | $\beta$ | 36.2 | 36.7 |
| Ser$^2$ | $\alpha$ | 55.9 | 55.9 | Tyr$^7$ | $\alpha$ | 55.7 | 55.8 |
| | $\beta$ | 61.4 | 61.4 | | $\beta$ | 36.3 | 36.2 |
| Thr$^3$ | $\alpha$ | 59.3 | 59.3 | | $\gamma$ | 127.9 | 128.0 |
| | $\beta$ | 67.2 | 67.3 | | $\delta, \delta'$ | 130.7 | 130.7 |
| | $\gamma$ | 19.0 | 19.0 | | $\epsilon, \epsilon'$ | 115.8 | 115.9 |
| Thr$^4$ | $\alpha$ | 59.3 | 59.3 | | $\zeta$ | 154.8 | 154.9 |
| | $\beta$ | 67.3 | 67.3 | Thr$^8$ | $\alpha$ | 59.0 | 59.1 |
| | $\gamma$ | 19.0 | 19.0 | | $\beta$ | 67.3 | 67.2 |
| Thr$^5$ | $\alpha$ | 59.3 | 59.3 | | $\gamma$ | 19.0 | 19.0 |
| | $\beta$ | 67.3 | 67.4 | | | | |
| | $\gamma$ | 19.0 | 19.0 | | | | |

| | | C-1 | C-2 | C-3 | C-4 | C-5 | C-6 |
|---|---|---|---|---|---|---|---|
| 31 | $\alpha$-D-glucopyranosyl | 99.9 | 72.0 | 76.8 | 69.7 | 73.2 | 60.8 |
| | $\beta$-D-glucopyranose | 79.3 | 72.0 | 77.2 | 76.4 | 72.9 | 60.8 |

$^a$15.0 mg in 10% CD$_3$COOD/H$_2$O (600 mm³, pH 2.72).
$^b$4.6 mg in 10% CD$_3$COOD/H$_2$O (600 mm³, pH 2.41).

REFERENCES

1. Merrifield, R. B. (1963), J. Am. Chem. Soc., 85, 2149–2153.
2. Barany G. and Merrifield R. B. (1979) in The Peptides, Vol. 2 (Academic Press, N.Y.) 1–284.
3. [a]Atherton, E., Clive, D. L. J. and Sheppard, R. C. (1975), J. Am. Chem. Soc., 97, 6584–6585; [b]Arshady, R., Atherton, E., Clive, D. L. J. and Sheppard, R. C., J. Chem. Soc., Perkin Trans. 1, 1981, 529–537.
3. Atherton, E., Fox, H., Harkiss, D., Logan, C. J., Sheppard, R. C. and Williams, B. J., J. Chem. Soc., Chem. Commun., 1978, 537–539.
5. Chang, C. D. and Meienhofer, J. (1978), Int. J. Peptide Protein Res. 11, 246–249.
6. Atherton, E., Brown, E., Sheppard, R. C. and Rosevear, A., J. Chem. Soc., Chem. Commun., 1981, 1151–1152.
7. Small, P. W., and Sherrington, D. C., J. Chem. Soc., Chem. Commun., 1989, 1589–1591.
8. Rapp, W., Zhang, L., Häbich, R. and Bayer, E. (1988) in Peptides, Proc. of 20'th Eur. Pept. Symp., (Jung, G. ed., 1989 Walter de Gruyter and Co., Berlin) 199–201.
9. Zalipsky, S., Albericio, F. and Barany, G. (1985) in Peptides: Structure and Function, Proc. of 9'th Am. Pept. Symp. (Deber, C. M., Hruby, V. J., Kopple, K. D. eds., Pierce Chemical Company, Illinois) 257–260.
10. Berg, R., Amdal, K., Pedersen, W. B., Holm, A., Tam, J. P. and Merrifield R. B. (1989), J. Am. Chem. Soc., III, 8024–8026.
11. Daniels, S. B., Bernatowicz, M. S., Coull, J. M. and Köster, H. (1989), Tetrahedron Lett., 30, 4345–4348.
12. Eichler, J., Beinert, A., Stierandova, A. and Lebl, M. (1991), Peptide Research, 4, 296–307.
13. Trijasson, P., Frere, Y., and Gramain, P., Makromol. Chem., Rapid Commun., 1990, 11, 239–243.
14. Kanda, P., Kennedy, R. C. and Sparrow, J. T. (1991), Int. J. Pept. Prot. Res., 38, 385–391.
15. Rink, H. (1987), Tetrahedron Lett., 28, 3787–3790.
16. Knorr, R., Trzeciak, A., Bannwarth, W., and Gillessen, D. (1989), Tetrahedron Lett. 30, 1927–1930.
17. Atherton, E., Holder, J. L., Meldal, M., Sheppard, R. C., and Valerio, R. M., J. Chem. Soc., Perkin Trans. 1, 1988, 2887–2894.
18. Cameron, L. R., Holder, J. L., Meldal, M. and Sheppard, R. C., J. Chem. Soc., Perkin Trans. 1, 1988, 2895–2901.
19. Cameron, R. L., Meldal, M. and Sheppard, R. C., J. Chem. Soc., Chem. Commun., 1987, 270–272. The reaction times are twice that observed visually, matching the sensitivity and reaction times as observed with the solid phase spectrophotometer.
20. Atherton, E. and Sheppard, R. C. (1989) in Solid Phase Peptide Synthesis, A Practical Approach (IRL, Oxford University Press, Oxford), 63–86.

I claim:

1. A crosslinked poly(ethylene or propylene) glycol-containing polymer formed by radical copolymerization of a derivatived poly(ethylene or propylene) glycol of the formula

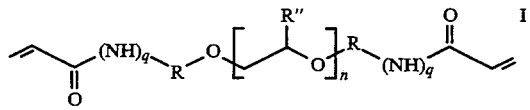

wherein
a) n is an integer of from 4 to 2,000,
b) R″ is H or $CH_3$,
c) R is $—(CR'_2)_s—(C_6R'_6)_t—(CR'_2)_u—$ wherein each R′ is H, alkyl, aralkyl, substituted aralkyl, aryl or substituted aryl, said substituted aralkyl and substituted aryl being ring substituted with alkyl, hydroxy, mercapto, nitro, amino, mono- or dialkylamino, or halogen;
d) q is zero or 1 and s, t and u each is zero or an integer of 1–10, provided that the polymer contains no ester bonds, with an acrylic compound of the formula

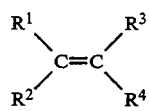

wherein $R^1$ is $—CY—X—R^5$ or $—CN$, and $R^2$, $R^3$ and $R^4$ each is H, alkyl, aralkyl, aryl, $—CY—X—R^5$ or $—CN$, where Y is O or S, X is O, S or $NR^6$, $R^5$ is alkyl, aralkyl or aryl, and $R^6$ is H or $H^5$.

2. A polymer according to claim 1, wherein the copolymerization has further included a spacer molecule comprising functional groups for the attachment of peptides, proteins, nucleotides or saccharides.

3. A polymer according to claim 2 which incorporates a spacer comprising functional groups selected from the group consisting of amino, alkylamino, hydroxy, carboxyl, mercapto, sulfeno, sulfino, sulfo and derivatives thereof.

4. A polymer according to claim 2 which is formed by copolymerization of a derivatized poly(ethylene or propylene) glycol of the formula I, wherein n, q, R″ and R are as defined in claim 1, with an acrylamide of the formula

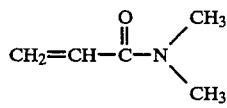

and with a spacer molecular of the formula

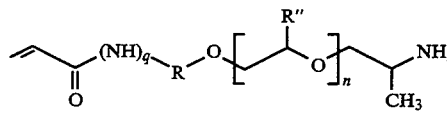

wherein n, q, R″ and R are as defined for formula I in claim 1.

5. A polymer according to claim 4 which is composed of 60% of 0,0′-bis-(2-acrylamidoprop-1-yl)-$PEG_{1900}$ (1), 20% of 0-(2-acrylamidoprop-1-yl)-0′-(2-aminoprop-1-yl)-$PPG_{300}$(2) and 20% of N,N-dimethyl acrylamide (3).

6. A polymer according to claim 4 derivatized with any of the linkers normally used in peptide synthesis.

7. A polymer according to claim 6 said linker being 4-[fluorenylmethyloxycarbamido(2,4-dimethoxyphenyl)methyl]phenoxyacetic acid of the formula

4-hydroxymethylphenoxyacetic acid, 4-hydroxymethylbenzamide or 4-hydroxymethyl-3-nitrobenzamide.

8. A solid support for continuous flow or batchwise synthesis of peptides said support comprising a polymer according to claim 1.

9. A solid support for continuous flow or batchwise synthesis of oligonucleotides said support comprising a polymer according to claim 1.

10. A solid support for the synthesis of oligosaccharides said support comprising a polymer according to claim 1.

11. A solid support according to claim 1 said support being suitable for synthesis by enzymatic reactions.

12. A solid support according to claim 10 for enzymatic synthesis of oligosaccharides with glycosyltransferases.

13. A solid support for the immobilization of proteins said support comprising a polymer according to claim 1.

14. A resin for application in chromatographic separations said resin comprising a polymer according to claim 1.

15. A method of continuous flow or batchwise synthesis of a peptide wherein the peptide during the synthesis is attached to a solid support comprising a polymer according to claim 1 and at the end of the synthesis is cleaved from said solid support.

16. A method of continuous flow or batchwise synthesis of an oligonucleotide wherein the oligonucleotide during the synthesis is attached to a solid support comprising a polymer according to claim 1 and at the end of the synthesis is cleaved from said solid support.

17. A method of continuous flow or batchwise synthesis of an oligosaccharide wherein the oligosaccharide during the synthesis is attached to a solid support comprising a polymer according to claim 1 and at the end of the synthesis is cleaved from said solid support.

18. A method according to claim 1 wherein the synthesis involves an enzymatic reaction.

19. A method according to claim 17 for enzymatic synthesis of an oligosaccharide with a glycosyltransferase.

20. A method of immobilizing a protein wherein the protein is attached to a solid support comprising a polymer according to claim 1.

21. A method of performing chromatographic separations which comprises the use of a chromatographic resin comprising a polymer according to claim 1.

* * * * *

UNITED STATES PATENT AND TRADEMARK OFFICE
CERTIFICATE OF CORRECTION

PATENT NO. : 5,352,756
DATED : October 4, 1994
INVENTOR(S) : Morten P. MELDAL

It is certified that error appears in the above-indentified patent and that said Letters Patent is hereby corrected as shown below:

On the title page, left column item 54, "Propylene" should be --Propylene)-- and "Glycol)" should be --Glycol--.

Column 12, line 30 (claim 1, line 34), "$H^5$" should be --$R^5$--.

Signed and Sealed this

Seventh Day of February, 1995

Attest:

BRUCE LEHMAN

Attesting Officer    Commissioner of Patents and Trademarks